United States Patent [19]

Martinez

[11] Patent Number: 4,971,023
[45] Date of Patent: Nov. 20, 1990

[54] DUAL COMPARTMENT INDUCED CIRCULATION OVEN

[75] Inventor: Cesar G. Martinez, San Antonio, Tex.

[73] Assignee: Roto-Flex Oven Company, San Antonio, Tex.

[21] Appl. No.: 326,750

[22] Filed: Mar. 21, 1989

[51] Int. Cl.⁵ .............................................. F24C 15/32
[52] U.S. Cl. ................................. 126/21 R; 126/299 R; 126/312
[58] Field of Search ............ 126/299 R, 299 D, 19 R, 126/21 R, 21 A, 299 F, 273 R, 20, 307 R, 312; 34/220, 221, 201, 225; 98/115.1, 115.3, 115.4; 55/DIG. 36; 219/399, 400

[56] References Cited

U.S. PATENT DOCUMENTS

| | | | |
|---|---|---|---|
| 1,802,617 | 4/1931 | Mullin et al. | 126/299 R |
| 2,564,087 | 8/1951 | Warren | 126/299 R |
| 2,595,480 | 5/1952 | Nelson et al. | 126/299 R |
| 4,592,333 | 6/1986 | Dustin | 126/299 R |

Primary Examiner—James C. Yeung

[57] ABSTRACT

A commercial or institutional oven with two separate oven compartments, individually controllable as to temperature. The oven compartments are ported and fanvented for providing even distribution of heat, smoke and steam, as applicable, while minimizing the expulsion of such cooking elements from the oven compartments. The porting and exhast system are shared by the two oven compartments in avoiding duplication of components. The exhaust system induces ventilation of the oven compartments through utilization of the venturi effect rather than through direct suction by way of a direct mechanical connection between the fan and each oven compartment's exhaust port. The design of the exhaust system permits use of a general purpose fan, as opposed to one designed for high temperature use.

16 Claims, 5 Drawing Sheets

DUAL COMPARTMENT INDUCED CIRCULATION OVEN

BACKGROUND OF THE INVENTION

1. Field of The Invention

Applicant's invention relates to large capacity ovens for commercial or institutional preparation of food.

2. Background Information

Presently, commercial or institutional food preparers, particularly of meats and breads, face high equipment costs, high utility costs, ovens which do not cook foods evenly throughout their cooking compartments, equipment space restrictions, and/or ovens which tend to overly dehydrate foods during the cooking process.

Commercial ovens available today are, at best, the products of compromise between the need for uniform heating, a low dehydration effect, and reasonable operating costs. Circulation of heat and air within an oven is necessary for uniform heating and may be achieved in currently available ovens. However, uniform heating is presently achieved by equipping ovens with large flues and/or fan-equipped vents to obtain the necessary circulation of heat and air within the cooking compartment. The result is a high volume flow of air through the oven's cooking compartment which tends to dehydrate food as well as escalate utility costs because of the great loss of heat. Equally troublesome is the fact that ovens which conserve energy and tend to lessen the dehydrating effect of cooking by retaining more of their heat do not tend to cook as evenly.

It would be desireable, therefore, to provide ovens for large scale preparation of foods which simultaneously cook foods uniformly throughout their cooking compartments, minimize dehydration of foods, and conserve energy. The ovens should ideally be designed for requiring a minimum of expensive components without sacrifice of quality or durability. Finally, it would be desireable for such ovens to be designed to effectively comprise two separate ovens, individually controllable as to cooking conditions, but which collectively require less space than two stand-alone ovens of like capacity.

SUMMARY OF THE INVENTION

It is an object of the present invention to provide a novel and useful commercial or institutional oven which cooks foods evenly.

It is another object of the present invention to provide a novel and useful commercial or institutional oven which simultaneously cooks foods evenly and reduces the rate of dehydration as compared with presently available ovens.

It is another object of the present invention to provide a novel and useful commercial or institutional oven which provides two separate oven compartments, individually controllable as to cooking conditions, but which collectively require less space than two stand-alone ovens.

It is an object of the present invention to provide a novel and useful commercial or institutional oven which conserves energy.

It is an object of the present invention to provide a novel and useful commercial or institutional oven designed for requiring a minimum of expensive components without sacrifice of quality or durability.

In satisfaction of these and related objectives, Applicant's invention provides a commercial or institutional oven with two separate oven compartments, individually controllable as to temperature and, optionally, as to other cooking conditions such as steam and smoke. The oven compartments are ported and fan-vented for providing even distribution of heat, smoke and steam, as applicable, while minimizing the expulsion of such cooking elements from the oven compartments. The porting and exhaust system are shared by the two oven compartments in avoiding duplication of components. The exhaust system induces ventilation of the oven compartments through utilization of the venturi effect rather than through direct suction by way of a direct mechanical connection between the fan and each oven compartment's exhaust port. The design of the exhaust system permits use of a general purpose fan, as opposed to one designed for high temperature use. Maintenance of the fan and the exhaust system is minimal because the fan components never come into direct, significant contact with the oven compartments' exhaust.

DETAILED DESCRIPTION OF THE PREFERRED EMBODIMENT

Figure 1:
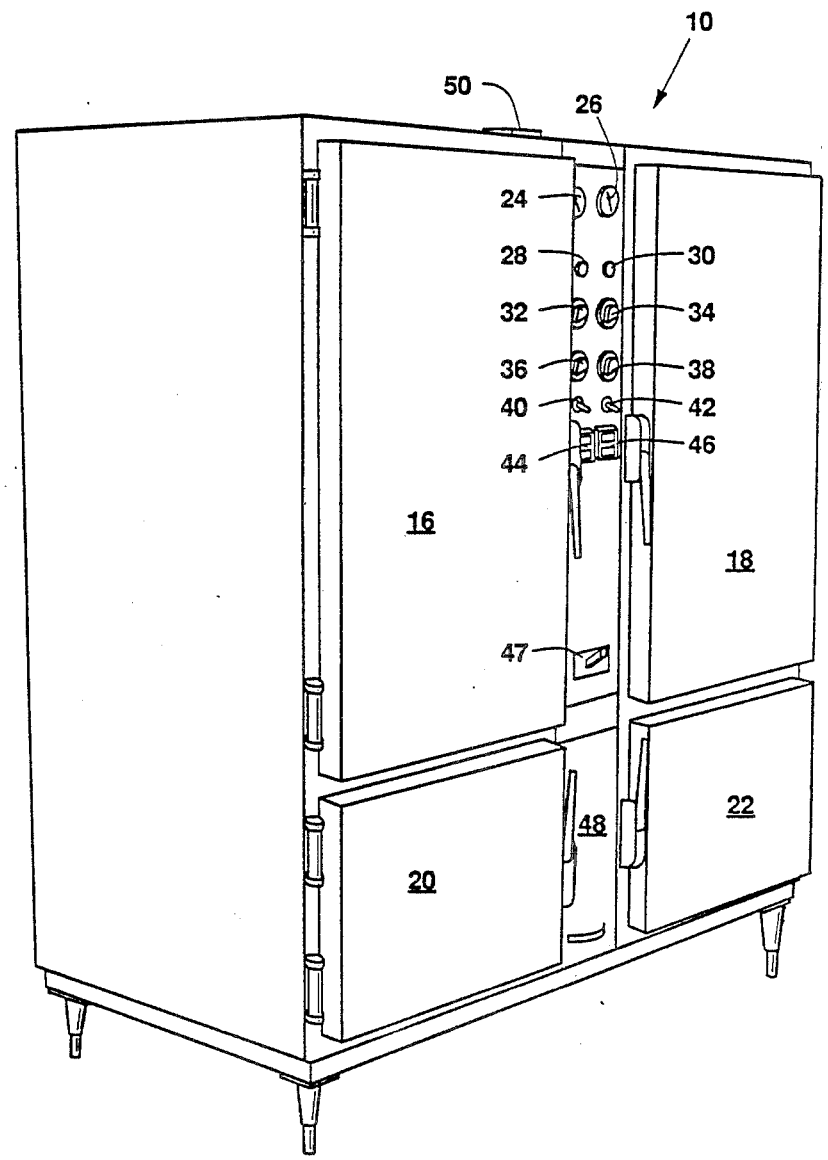
FIG. 1 is a perspective view of the preferred embodiment.

Referring in to FIG. 1, the preferred embodiment of Applicant's invention is shown to depict the overall arrangement thereof. The oven 10 has two oven compartments 12 and 14 (not visible in FIG. 1) respectively with hinged and latched insulated doors 16 and 18. Two additional doors 20 and 22 on the front of the oven 10 allow access to the heat generating means (to be shown and discussed hereinafter).

Referring still to FIG. 1, indicators and control actuators for the oven 10 comprise, respectively for oven compartments 12 and 14, thermometers 24 and 26, single pole on/off switches 28 and 30, primary burner thermostatic controls 32 and 34, booster burner thermostatic controls 36 and 38, double pole switches 40 and 42 with timer/manual positions, timer controls 44 and 46, and a main power switch 47.

Referring still to FIG. 1, a grease trap cover 48 is also situated at the front of the oven 10 to access a grease trap shown in other figures and to be discussed hereinafter. The external extension of the flue 50 is also visible in FIG. 1.

Although actual dimensions and positions of oven components are not considered controlling of any of its benefits (within the scope of ovens which are contemplated to be built according to Applicant's design) ratios of dimensions and/or positions of components are important. Therefore, actual dimensions and positions for Applicant's preferred embodiment will be indicated for certain components from which the appropriate ratios for alternatively sized units may be derived. Accordingly, the interior dimensions of the oven compartments 12 and 14 of Applicant's preferred embodiment are forty five inches by twenty four inches by thirty inches (H45"×W24"×D30"). Other dimensions will be indicated as appropriate.

Figure 2:
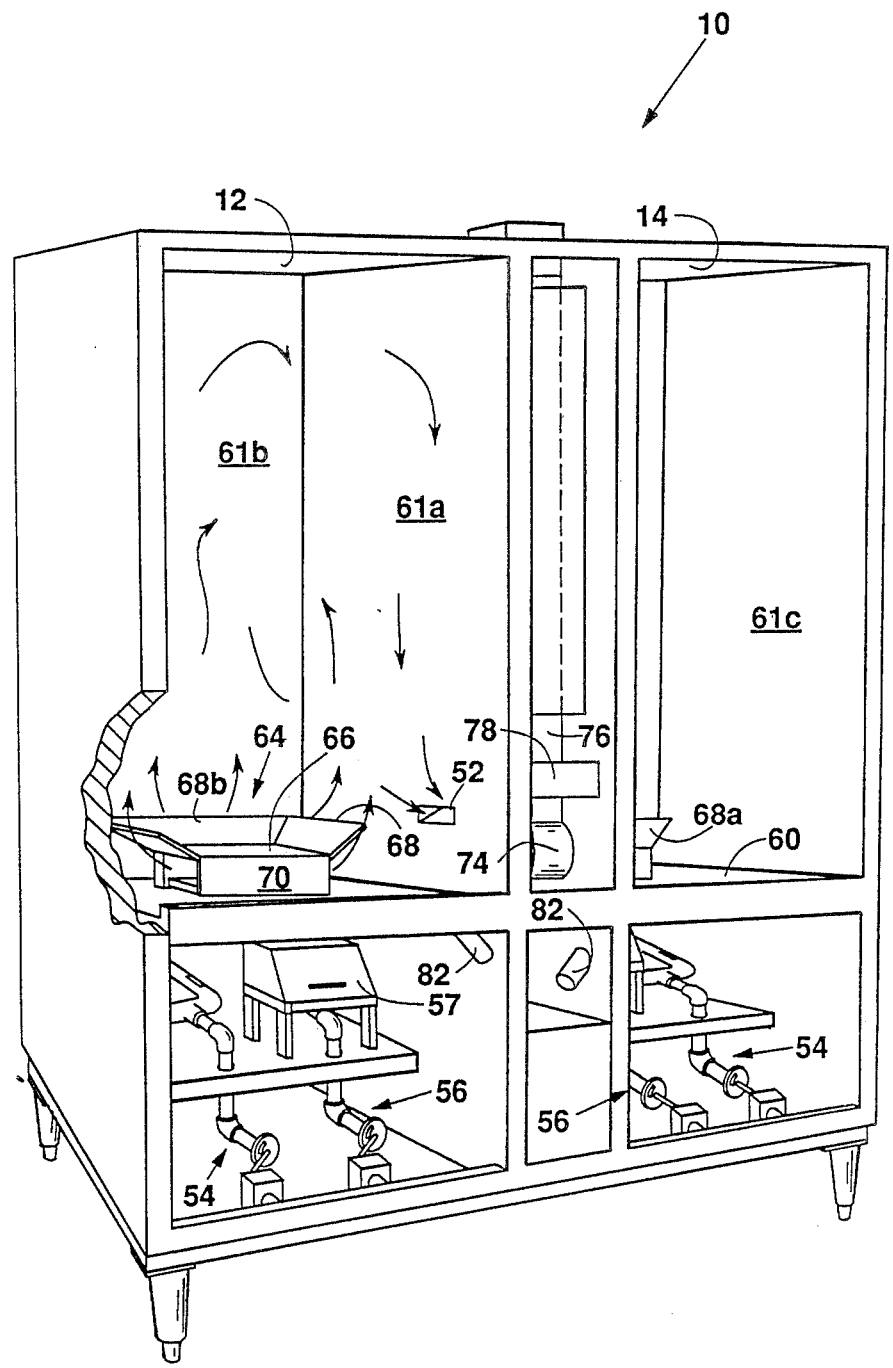
FIG. 2 is a partial cut-away perspective view of the preferred embodiment showing the interior of the oven compartments and visually depicting the course of heat into, through and from the oven compartments.
Figure 3:
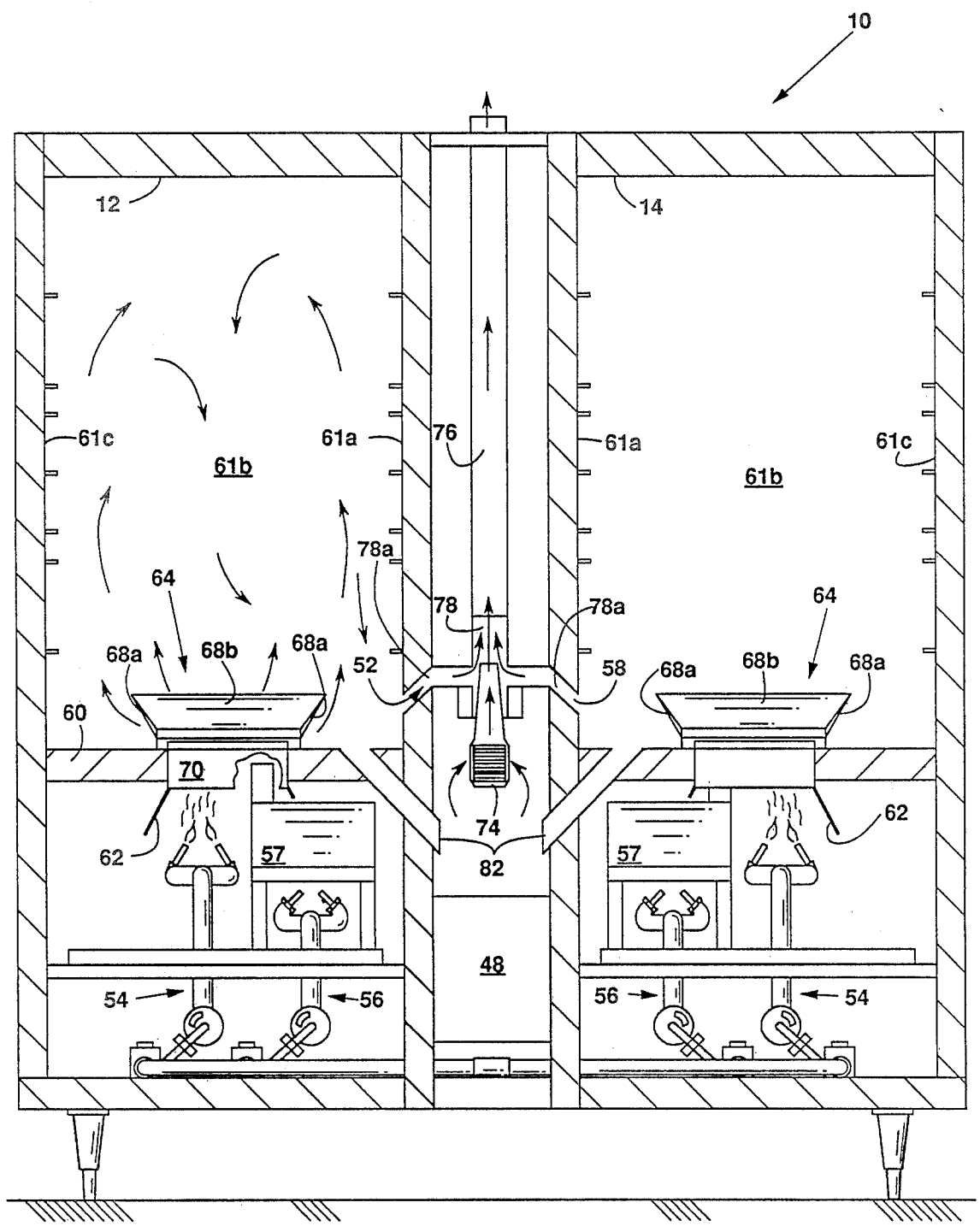
FIG. 3 is a cross sectional view of the preferred embodiment along Line —which depicts the internal components of the preferred embodiment and visually depicts the flow of feat into, through, and from the oven compartments.

Referring in combination to FIGS. 2 and 3, flow of heated air and associated steam and/or smoke through the oven compartments 12 and 14 is the result, as well as one of the primary objectives, of Applicant's design. The arrows shown in the FIGS. 2 and 3 are not meant to literally represent the flow of heated air though the oven compartments 12 and 14, but merely to indicate generally that such flow is into the oven compartments 12 and 14 from vents 58 in their respective floors 60, throughout their interior spaces, and out through their exhaust ports 52. Heat flow of this nature is important in achieving the uniform cooking which is sought by Applicant's design. The exhaust ports 52 are rectangular in shape, measure two inches by five inches (H2"×D5") and are situated on the interior wall 61a of each oven compartment 12 and 14. The center point of each exhaust port 52 is situated five and three fourth inches (4¾") above the oven floor 60 and twenty four and one-half inches (24½") from the oven rear wall 61b. This position for the exhaust ports 52 has been determined through exhaustive experimentation to provide the most desireable cooking uniformity for Applicant's preferred embodiment when combined with the other elements of Applicant's invention to be described herein. Although not depicted in the drawings, it is noted that moveable dampers may be installed to overlie the exhaust ports 52 and thereby allow fine adjustment of air exhaust flow by a user.

Referring still to FIGS. 2 and 3, each of the oven compartments 12 and 14 is heated by two natural gas or propane burner assemblies 54 and 56. The burner assemblies 54 and 56 are as typically used for commercial/institutional ovens. Burner assemblies 54 will be referred to as the primary burners 54 and the burner assemblies 56 are referred to as the booster burners 56. A removable chip box 57 is designed to be placed over the booster burners 56 of either or both oven compartments 12 and 14. Chip boxes 57 may be filled with appropriate wood shavings or pieces (not shown) and, once sufficiently heated by the booster burners 56, introduce smoke into the oven compartments 12 and/or 14.

Heat derived from the burners 54 and 56 (and smoke if applicable) pass into the oven compartments 12 and 14 through a vent 58 in each of the oven floors 60. The vents 58 are rectangular in shape and measure eight inches by thirteen inches (W8"×D13") with their narrow sides being parallel with the back walls 61b. The vents' 58 center points are positioned on the oven floors 60 nine and one-half inches (9½") from the rear wall 61b and twelve (12") from the interior walls 61a and exterior walls 61c. A one inch (1") vertically oriented flange 58a rises from the oven floor 60 and completely surrounds each vent 58.

Referring still to FIGS. 2 and 3, fins 62 extend from the underside of oven floors 60 and are directed generally downward from the oven floors 60 and outward from the center of the vents 58. The fins 62 serve to direct the substantial majority of the heat rising from the burners 54 and/or 56 through the vents 58.

A heat disperser 64 is placed over the vent 58 in each of the oven compartments 12 and 14 to disperse the heat from the burners 54 and/or 56. Each heat disperser 64 has a rectangular horizontal panel 66 which is, in the preferred embodiment, ten inches by thirteen and one-half inches (W10"×D13½"). Side heat disperser fins 68a extend upwardly and outwardly from each of the two broad sides of the horizontal panel 64 at an approximately twenty five degree (25) angle from the horizontal. The side heat disperser fins 68a are five and one-half inches in width (W5½") as measured in the plane defined by the fins 68a, from the adjoining broad side of the horizontal panel 66, and perpendicularly to their lengths. A rear disperser fin 68b extends upwardly and outwardly from the rear narrow side of the horizontal panel 66 at an approximately eighty degree (80) angle from the horizontal. The rear disperser fin 68b is approximately three inches in depth (D3") as measured in the plane defined by the rear disperser fin 68b, from the adjoining narrow side of the horizontal panel 66, and perpendicularly to its length.

No disperser fin is situated on the narrow side of the horizontal panel 66 closest to and parallel with the oven compartments' 12 and 14 door openings (not separately numbered). Instead, a vertical panel 70 extends perpendicularly and downward from the front narrow side of the horizontal panel 66 to rest on the oven compartment floor 60. The vertical panel 70 serves, not only to support the heat disperser 64, but to prevent heat from vent 58 from tending to travel directly into the exhaust port 52 rather than upward to circulate throughout the oven compartment 12 or 14 before exiting through the exhaust port 52.

Two disperser feet 72 are attached to the underside of the heat disperser 64 and support each heat disperser 64 on their respective oven floors 60. The disperser feet 72 are each approximately four inches (4") in length. This causes the horizontal panel 66 to tilt slightly from the horizontal whereby grease falling thereon rolls off onto the oven floor 60 to pass to the grease trap (to be discussed hereinafter).

When installed, each heat disperser 64 is centered over a vent 58 whereby the exterior edge of the rear disperser fin 68b is positioned one inch (1") from the rear oven wall 61b and the outermost edges of the side disperser fins 68a are positioned two inches (2") from the oven compartments' 12 and 14 side walls 61a and 61c.

The heat disperser 64 of the preferred embodiment as just described has proven optimal is dispersing heat within the oven compartments 12 and 14 when combined with the other features of the preferred embodiment, other positions and relative dimensions having proven substantially less effective.

Referring still to FIGS. 2 and 3, heat circulation within the oven compartments 12 and 14 is induced by an exhaust assembly which comprises the previously mentioned exhaust ports 52, a fan 74, an exhaust flue 76, and an exhaust manifold 78.

The exhaust manifold 78 is a member which includes conduits 78a between the exhaust ports 58 and the exhaust flue 76 and also supports the fan 74. The conduits 78a intersect the oven walls 61a at an approximate forty five degree (45) angle as shown to reduce the likelihood of water and cleaning solutions reaching the fan 74 during cleaning operations. The flue 76 is rectangular in horizontal cross section and measures four inches square (4"×4"). The fan 74 used for Applicant's preferred embodiment is a Dayton shaded pole blower which delivers 108 cfm free air at 1530 rpm at 60 Hz.

The fan 74 used for the preferred embodiment is Stock No. 2C067 as available from W. W. Grainger, Inc. who has distributors throughout the United States and abroad.

The precisely desired air flow was achieved by Applicant by fitting an air nozzle 80 to the effluent port of the fan 74 reducing its size from three and five-sixteenths inches by three and five-sixteenths inches (W3 5/16"×D3 5/16") to three inches by two and three eights inches (W3"×D2⅜"). In operation, the fan 74 forces air drawn from underneath the oven 10 up through the flue 76. In so doing, and by virtue of a venturi effect, the fan 74 causes a pressure drop in the flue 76 resulting in air being evacuated from the oven compartments 12 and 14 through the exhaust ports 52 and the conduits 78a.

By indirectly evacuating the oven compartments 12 and 14 as described, as opposed to doing so through suction supplied by a fan in direct mechanical connection with the exhaust ports 52, the fan 74 of Applicant's preferred embodiment need not be of the expensive variety designed for high temperature use. This is because the fan 74 of Applicant's preferred embodiment never actually contacts the heated air from the oven compartments 12 and 14. The dissociation of the fan 74 from the actual exhaust air provides a further benefit in allowing substantially less frequent cleaning of the fan 74 which would be necessary of any fan in direct contact with the humid, grease laden oven exhaust.

In addition to adjusting the air flow to the precisely desired velocity, the air nozzle 80 also serves to extend the effluent port of the fan 74 to a point above the conduits 78a. Optimum cooking conditions have been achieved by Applicant in so placing the effluent orifice of the fan 74. In this way, the forced, turbulent air from the fan 74 does not find its way into the oven compartments 12 and 14 thereby impeding the desired even circulation of heat and/or introducing cool air into the oven compartments 12 or 14. The gentle, even vacuum created by the exhaust assembly of the preferred embodiment promotes even, low-turbulence circulation of the heat and associated steam or smoke within the oven compartments 12 and 14.

Figure 4:
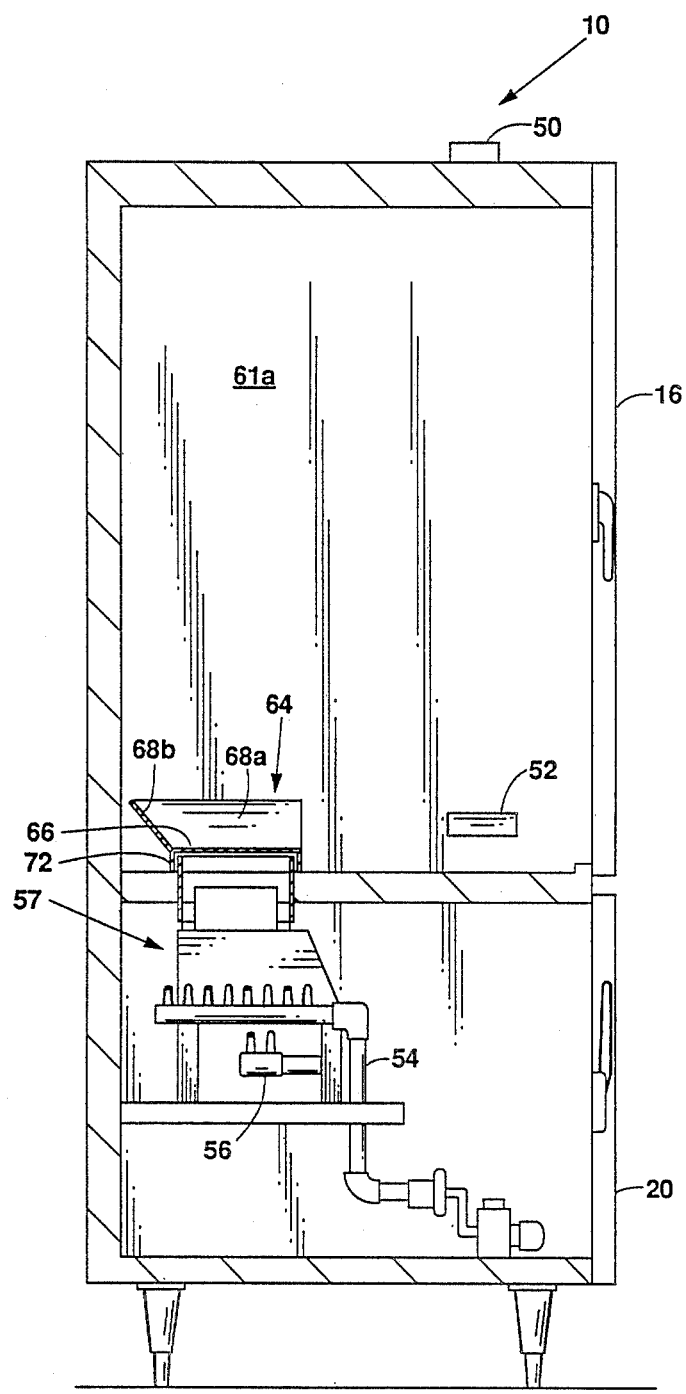
FIG. 4 is a cross sectional view of the preferred embodiment alone Line 13.

Referring in combination to FIGS. 3 and 4, a rim 61 is provided at the door edge of the oven floors 60 to contain grease and other fluids which fall to the oven floors 60 in combination with previously identified flange 58a. Such fluids then are carried to a receptacle (not separately identified) situated behind the grease trap cover 48 by conduits 82. The conduits 82 pass through the oven floors 60 and open into oven compartments 12 and 14 as shown. The flange 58a, the rim 61, the heat disperser 64, and the conduits 82 all combine to prevent grease from reaching the burners or accumulating on the oven floors 60 thereby creating a danger of combustion.

Figure 5:
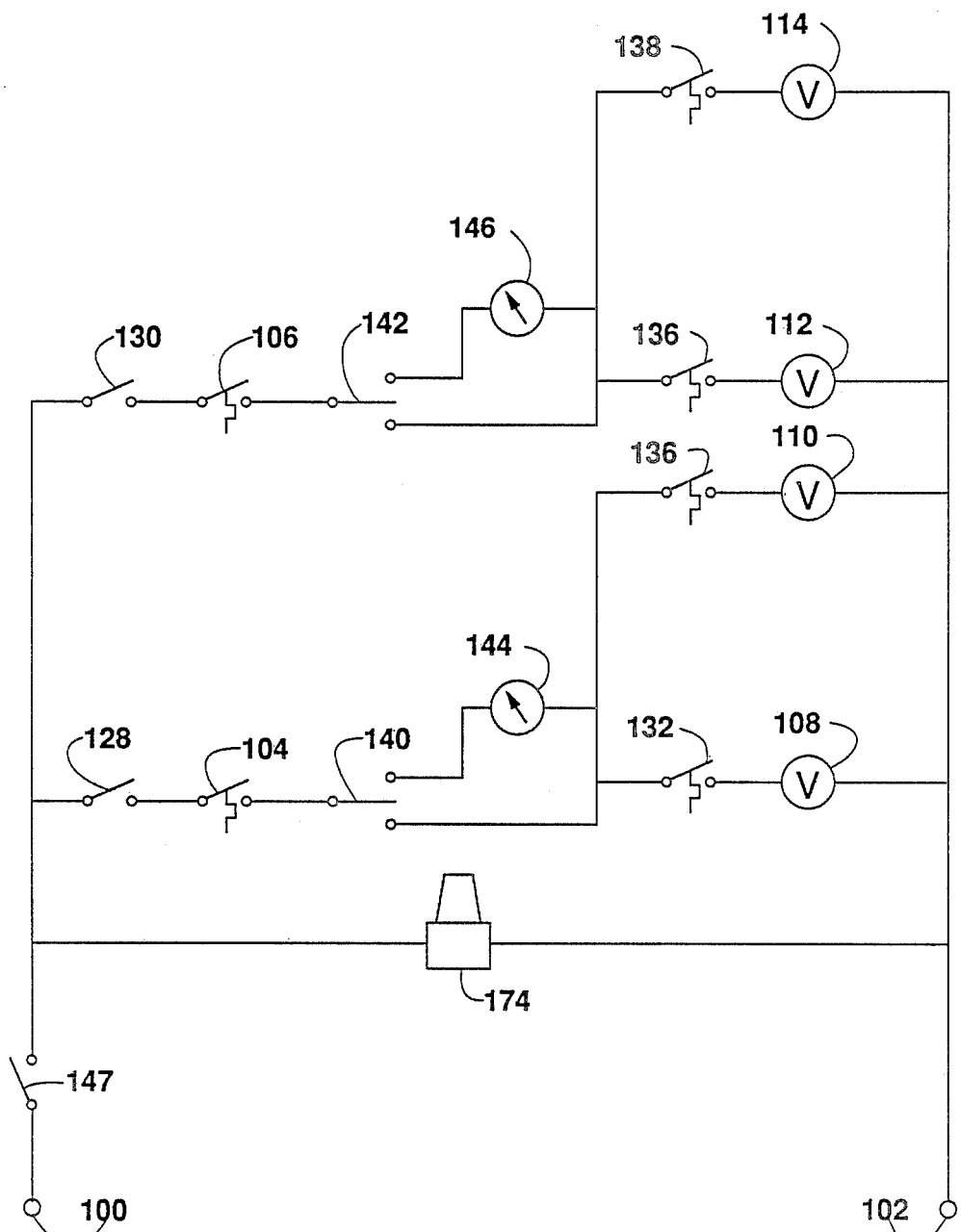
FIG. 5 is an electrical schematic of the electrical components of the preferred embodiment.

Referring to FIG. 5, the electrical components of Applicant's preferred embodiment are depicted in schematic form. Where components in their physical have been previously identified by a reference numeral, they are again identified in FIG. 5 using the same reference numeral, but preceded by a "1". The electrical components of the preferred embodiment include leads 100 and 102 for connection to a 120 VAC power supply, a master power switch 147, and the blower 174. The following components, respectively controlling oven compartments 12 and 14, are also included: single pole switches 128 and 130, high limit thermostatic breakers 104 and 106, double pole switches 140 and 142, timer controls 144 and 146, adjustable thermostatic controls 132 and 134 for control of primary burners 54, adjustable thermostatic controls 136 and 138 for control of booster burners 56, solenoid actuated gas valves 108 and 112 for primary burners 54, and solenoid actuated gas valves 110 and 114 for booster burners 56.

High limit thermostatic controls 104 and 106 are included as a safety measure and will interrupt operation of one or both of the oven compartments 12 and 14 if either exceeds a pre-set, break-off temperature. Although the circuitry depicted in FIG. 5 indicates the timer controls 144 and 146 as simultaneously controlling their respective primary burners 54 and booster burners 56, minor modification of circuitry along with the use of dual control timers would allow separate control of the primary burners 54 and booster burners 56. This would be particularly advantageous as, for example, when a user would like to maintain a certain elevated temperature using the primary burners 54 for a designated time period, and thereafter, maintain a lower holding temperature using the booster burners 56. One skilled in the art may make such modifications and necessary substitutions of components without necessary further disclosure herein.

The benefits of Applicant's novel design are several. The heat and air circulation within the oven compartments 12 and 14 achieved by Applicant's design provides extremely uniform heating throughout the compartments' 12 and 14, but not at the cost a large flux of air and heat through the system with the associated high rate of dehydration and high operating costs. Also, because the single exhaust assembly of Applicant's design is suitable for the two separate oven compartments 12 and 14, the flexibility and convenience of two independently controllable ovens is achieved with little more additional space requirements than are necessary to accommodate the volume of the actual second oven compartment. As mentioned above, the design of the exhaust assembly also minimizes component cost and maintenance requirements.

Although the invention has been described with reference to specific embodiments, this description is not meant to be construed in a limited sense. Various modification of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

I claim:

1. An oven comprising:
   heating means;
   a first oven compartment;
   an exhaust port situated in a wall of said oven compartment;
   a flue;
   an exhaust conduit connected to said first oven compartment at said exhaust port and to said flue whereby said first oven compartment and said flue are in spatial communication; and
   fan means situated relative to said flue for propelling air through said flue;
   said first oven compartment is box-like in shape having first, second, third and fourth vertical faces and first and second horizontal faces with a door member said first vertical face, said exhaust port being formed in said second vertical face which intersects said first face and being centered on a point approximately four-fifths of the distance from said third on vertical face which is opposite said first face and approximately five sixths of the distance from said first and uppermost horizontal face of said oven.

2. An oven comprising:
a first oven compartment with first heating means associated therewith;
an exhaust port situated in a wall of said oven compartment;
a flue;
an exhaust conduit connected to said first oven compartment at said exhaust port and to said flue whereby said first oven compartment and said flue are in spatial communication; and
fan means situated relative to said flue for propelling air through said flue;
said first oven compartment is box-like in shape having an upper and a lower horizontal wall, first and second vertical side walls, a vertical rear wall, ad a door member for closing said first oven compartment at said first oven compartment's remaining face there being no wall at said remaining face, said exhaust port being formed in said first side wall and being centered on a point approximately four-fifths of the distance from said rear wall to said door member and approximately five sixths of the distance from said oven's upper wall to said lower wall.

3. The invention of claim 2 wherein said flue is vertically oriented and situated substantially parallel with the lines of intersection of said side walls and said rear wall of said first oven compartment, said flue being in the nature of a conduit with a first lower open end and second upper open end and otherwise sealed except as intercepted by said exhaust conduit, said exhaust conduit intercepting said flue near said first lower end in a relative orientation approximately perpendicular to said flue's length.

4. The invention of claim 3 further comprising a framework for supporting components of said oven and wherein said fan means are mounted on said framework and positioned in proximity of said flue whereby the effluent port of said fan means is directed into said first open end of said flue and air flow from said fan means is directed generally parallel with said flue's length.

5. The invention of claim 4 wherein said lower wall has a heat orifice formed therethrough, said heat orifice being centered on a point approximately one third of the distance from said rear vertical wall to said door member and approximately equidistant between said vertical side walls, said orifice for passing heat from said heating means into said first oven compartment.

6. The invention of claim 5 wherein said heat orifice is substantially rectangular and further comprising a heat dispenser positioned over said heat orifice for uniformly dispersing heat from said heating means into said first oven compartment.

7. The invention of claim 6 wherein said heat disperser has a horizontal disperser panel of substantially similar dimensions as said heat orifice, first and second side heat disperser fins extending upwardly and outwardly, relative to said lower oven wall, from the two sides of said horizontal disperser panel oriented parallel with said first and second side walls, a rear heat disperser fin extending upwardly and outwardly, relative to said lower oven wall, from the side of said horizontal dispenser panel oriented parallel with said rear wall, support means for positioning said horizontal disperser panel several inches above said heat orifice, and a front deflector panel which extends downward from said horizontal disperser panel toward said lower wall to a level in close proximity but not in contact with said lower wall.

8. The invention of claim 7 wherein said heat means comprises a first gas or propane burner, said first burner being fueled by way of an electrically actuated valve in turn controlled by adjustable thermostatic means whereby temperature within said first oven compartment may be controlled.

9. The invention of claim 8 further comprising a second gas or propane burner, said second burner being fueled by way of an electrically actuated valve in turn being controlled by adjustable thermostatic means.

10. An oven comprising:
a first oven compartment with first heating means associated therewith;
a second oven compartment with second heating means associated therewith;
a first exhaust port situated in a wall of said first oven compartment;
a second exhaust port situated in a wall of said second oven compartment;
a flue;
a first exhaust conduit connected to said first oven compartment at said first exhaust port and to said flue whereby said first oven compartment and said flue are in spatial communication;
a second exhaust conduit connected to said second oven compartment at said second exhaust port and to said flue whereby said second oven compartment and said flue are in spatial communication; and
fan means situated relative to said flue for propelling air through said flue;
said first and second oven compartments are box-like in shape each having an upper and a lower horizontal wall, first and second vertical side walls, a vertical rear wall, and a door member for closing said first oven compartment at said first oven compartment's remaining face there being no wall at said remaining face, the respective said exhaust port of each said compartment being formed in said first side wall of the respective said oven compartment and being centered on a point approximately four-fifths of the distance from said rear wall to said respective door member and approximately five sixths of the distance from the respective upper wall to said lower wall.

11. The invention of claim 10 wherein said flue is vertically oriented and situated substantially parallel with the lines of intersection of said side walls and said rear wall of said first and second oven compartments, said flue being in the nature of a conduit with a first lower open end and second upper open end and otherwise sealed except as intercepted by said first and second exhaust conduits, said first and second exhaust conduits intercepting said flue near said first lower end in a relative orientation approximately perpendicular to said flue's length.

12. The invention of claim 11 wherein said lower walls of said first and second oven compartments each has a heat orifice formed therethrough, said heat orifices being centered on a point approximately one third of the distance from the respective said rear vertical wall to the respective said door member and approximately equidistant between the respective said vertical side walls, said heat orifices for passing heat respectively from said first and second heating means into said first and second oven compartments.

13. The invention of claim 12 wherein said heat orifices are substantially rectangular and further comprising first and second heat dispersers positioned respectively over said heat orifices for uniformly dispersing heat from said heating means into said oven compartments.

14. The invention of claim 13 wherein said heat dispersers each have a horizontal disperser panel of substantially similar dimensions as said heat orifices, first and second side heat disperser fins extending upwardly and outwardly, relative to their respective said lower oven walls, from the two sides of said horizontal disperser panel oriented parallel with their respective said first and second side walls, a rear heat disperser fin extending upwardly and outwardly, relative to their respective said lower oven wall, from the side of said horizontal disperser panel oriented parallel with their respective said rear wall, support means for positioning said horizontal disperser panel several inches above their respective said heat orifices, and a front deflector panel which extends downward from said horizontal disperser panel toward their respective said lower wall to a level in close proximity but not in contact with said lower wall.

15. An oven comprising:
a framework for supporting components of said oven; heating means;
a box-shaped first oven compartment having an upper and a lower horizontal wall, first and second vertical side walls, a vertical rear wall, and a door member for closing said first oven compartment at said first oven compartment's remaining face there being no wall at said remaining face, said lower wall having a substantially rectangular heat orifice formed therethrough, said heat orifice being centered on a point approximately one third of the distance from said rear vertical wall to said door member and approximately equidistant between said vertical side walls, said orifice for passing heat from said heating means into said first oven compartment;
an exhaust port being formed in said first side wall and being centered on a point approximately four-fifths of the distance from said rear wall to said door member and approximately five sixths of the distance from said oven's upper wall to said lower wall;
a flue, said flue being vertically oriented and situated substantially parallel with the lines of intersection of said side walls and said rear wall of said first oven compartment, said flue being in the nature of a conduit with a first lower open end and second upper open end and otherwise being sealed except as intercepted by an exhaust conduit, said exhaust conduit intercepting and being connected to said flue near said first lower end in a relative orientation approximately perpendicular to said flue's length, said exhaust conduit also being connected to said first oven compartment at said exhaust port bringing the interior of said first oven compartment into spatial communication with the interior of said flue;

fan means situated relative to said flue for propelling air through said flue, said fan means being mounted on said framework and positioned in proximity of said flue whereby the effluent port of said fan means is directed into said first open end of said flue and air flow from said fan means is directed generally parallel with said flue's length; and
a heat disperser positioned over said heat orifice for uniformly dispersing heat from said heating means into said first oven compartment, said heat disperser having a horizontal disperser panel of substantially similar dimensions as said heat orifice, first and second side heat disperser fins extending upwardly and outwardly, relative to said lower oven wall, from the two sides of said horizontal disperser panel oriented parallel with said first and second side walls, a rear heat disperser fin extending upwardly and outwardly, relative to said lower oven wall, from the side of said horizontal disperser panel oriented parallel with said rear wall, support means for positioning said horizontal disperser panel several inches above said heat orifice, and a front deflector panel which extends downward from said horizontal disperser panel toward said lower wall to a level in close proximity but not in contact with said lower wall.

16. An oven comprising:
a framework for supporting components of said oven;
primary oven heating means;
secondary oven heating means;
a box-shaped primary oven compartment having an upper and a lower primary oven horizontal wall, first and second vertical primary oven side walls, a vertical primary oven rear wall, and a primary oven door member for closing said primary oven compartment at said primary oven compartment's remaining face there being no wall at said remaining face, said primary oven lower wall having a substantially rectangular primary oven heat orifice formed therethrough, said primary oven heat orifice being centered on a point approximately one third of the distance from said rear primary oven wall to said primary oven door member and approximately equidistant between said primary oven side walls, said primary oven heat orifice being for passing heat from said primary oven heating means into said primary oven compartment;
a primary oven exhaust port being formed in said first primary oven side wall and being centered on a point approximately four-fifths of the distance from said primary oven rear wall to said primary oven door member and approximately five sixths of the distance from said primary oven upper wall to said primary oven lower wall;
a box-shaped secondary oven compartment having an upper and a lower secondary oven horizontal wall, first and second vertical secondary oven side walls, a vertical secondary oven rear wall, and a secondary oven door member for closing said secondary oven compartment at said secondary oven compartment's remaining face there being no wall at said remaining face, said secondary oven lower wall having a substantially rectangular secondary oven heat orifice formed therethrough, said secondary oven heat orifice being centered on a point approximately one third of the distance from said rear secondary oven wall to said secondary oven door member and approximately equidistant between said secondary oven side walls, said secondary oven heat orifice for passing heat from said secondary oven heating means into said secondary oven compartment;

a secondary oven exhaust port being formed in said second secondary oven side wall and being centered on a point approximately four-fifths of the distance from said secondary oven rear wall to said secondary oven door member and approximately five sixths of the distance from said secondary oven upper wall to said secondary oven lower wall;

a flue, said flue being vertically oriented and situated substantially parallel with the lines of intersection of said primary and secondary oven side walls and said primary and secondary oven rear walls, said flue being in the nature of a conduit with a first lower open end and second upper open end and otherwise being sealed except as intercepted by primary and secondary oven exhaust conduits, said primary and secondary oven exhaust conduits opening into and being connected to said flue near said first lower end in a relative orientation approximately perpendicular to said flue's length, said primary and secondary oven exhaust conduits also being respectively connected to and opening into said primary and secondary oven compartments at their said primary and secondary exhaust ports bringing the interior of said primary and secondary oven compartments into spatial communication with the interior of said flue;

fan means situated relative to said flue for propelling air through said flue, said fan means being mounted on said framework and positioned in proximity of said flue whereby the effluent port of said fan means is directed into said first open end of said flue and air flow from said fan means is directed generally parallel with said flue's length; and first and second heat dispersers respectively positioned over said primary and secondary oven heat orifices for uniformly dispersing heat from said first and second heating means into said primary and secondary oven compartments, said heat dispersers each having a horizontal disperser panel of substantially similar dimensions as said heat orifice, first and second side heat disperser fins extending upwardly and outwardly, relative to said lower oven walls, from the two sides of said horizontal disperser panel oriented parallel with said primary and secondary oven first and second side walls, a rear heat disperser fin extending upwardly and outwardly, relative to said lower oven walls, from the side of said horizontal disperser panel oriented parallel respectively with said primary and secondary oven rear walls, support means for positioning said horizontal disperser panels several inches above respective said primary and secondary oven heat orifice, and a front deflector panel which extends downward from said horizontal disperser panels toward said respective primary and secondary oven lower walls to a level in close proximity but not in contact with said lower walls.

* * * * *